United States Patent [19]
Webb

[11] Patent Number: 6,144,304
[45] Date of Patent: Nov. 7, 2000

[54] METHODS AND APPARATUS FOR THE SECURE IDENTIFICATION OF INFANTS AND PARENTS IN HEALTH CARE INSTITUTIONS

[76] Inventor: Nicholas J. Webb, P.O. Box 831, Wrightwood, Calif. 92397

[21] Appl. No.: 09/248,019

[22] Filed: Feb. 10, 1999

Related U.S. Application Data

[63] Continuation of application No. 08/733,763, Oct. 18, 1996, abandoned, which is a continuation-in-part of application No. 08/515,856, Aug. 16, 1995, Pat. No. 5,608,382.

[51] Int. Cl.[7] .................................................. G08B 23/00
[52] U.S. Cl. ........................ 340/573.4; 235/375; 283/75; 340/825.34
[58] Field of Search .............................. 340/573.4, 691.1, 340/825.34, 825.31, 825.32; 235/380, 382, 382.5, 375; 379/38, 40; 283/75; 40/633

[56] References Cited

U.S. PATENT DOCUMENTS

| | | | |
|---|---|---|---|
| 3,848,112 | 11/1974 | Weichselbaum et al. | 235/375 |
| 3,965,589 | 6/1976 | McDermott | 40/633 |
| 4,328,978 | 5/1982 | McLaughlin | 283/75 |
| 4,628,193 | 12/1986 | Blum | 235/375 |
| 5,006,830 | 4/1991 | Merritt | 340/573 |
| 5,266,783 | 11/1993 | McAllister | 235/382 |
| 5,423,574 | 6/1995 | Forte-Pathroff | 283/75 |
| 5,608,382 | 3/1997 | Webb et al. | 340/573 |

OTHER PUBLICATIONS

Godwin et al., "Taking Charge", RN, pp. 17–20, May 1991.
Dextradeur et al., "A Badge of Security", MCN, vol. 16, pp. 175–176, unknown.
Renner et al., "Wristband Identification Error Reporting in 712 Hospitals", Arch. Pathol. Lab. Med., vol. 117, p. 573, Jun. 1993.
Davis, "Other Precautions to Protect Newborns", RN, p. 13, Mar. 1992.
Advertisement for Touch Probe™ portable data collector, unknown.
Brochure for "Touch the Future" Automatic Identification, Dallas Semiconductor, unknown.
Touch Memory Starter Kit User's Manual, Dallas semiconductor, Jul. 1991.

*Primary Examiner*—Thomas Mullen
*Attorney, Agent, or Firm*—David P. Gordon; David S. Jacobson; Thomas A Gallagher

[57] ABSTRACT

A parent-infant identification system includes a matched set of three bracelets each bearing matching visual indicia and an electronically readable data button and a data button reading apparatus. Two of the three bracelets are sized to fit adult wrists and the third bracelet is sized to fit an infant wrist or ankle. The matching visual indicia preferably includes a color code. The data buttons each contain electronically readable data which allows the data buttons to be identified with the data button reader. The data button reading apparatus includes an audible signal apparatus for signalling whether or not the data buttons match, and recording apparatus for recording the results of button readings. According to a presently preferred embodiment of the invention, the electronically readable data in each data button includes data which identifies whether the button is attached to a parent bracelet or an infant bracelet. The data button on the infant bracelet contains matching data for matching the infant bracelet with the parent bracelets and the matching data is encrypted. The data buttons on the parent bracelets each includes the matching data for matching them with the infant bracelet data button as well as password data needed for reading the encrypted data on the infant data button.

10 Claims, 8 Drawing Sheets

FIG.8a
$202 \to 0\underbrace{1234}_{204}\underbrace{0000}_{206}$
FIG.8b
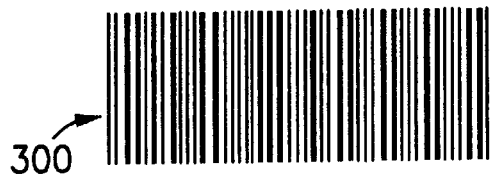
FIG.8c
$302 \to 0\underbrace{5678}_{304}\underbrace{0000}_{306}$
FIG.8d
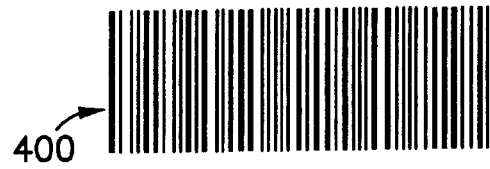
FIG.8e
$402 \to 1\underbrace{\overbrace{\underbrace{1234}_{204}\underbrace{5678}_{304}}^{404}}$
FIG.8f

METHODS AND APPARATUS FOR THE SECURE IDENTIFICATION OF INFANTS AND PARENTS IN HEALTH CARE INSTITUTIONS

This application is a continuation of application Ser. No. 08/733,763, filed Oct. 18, 1996, now abandoned, which is a continuation-in-part of application Ser. No. 08/515,856, filed Aug. 16, 1995, now U.S. Pat. No. 5,608,382.

BACKGROUND OF THE INVENTION

1. Field of the Invention

The invention relates to identification bracelets worn by infants and parents, which are used in hospitals to identify parents and infants as being members of the same family. More particularly, the invention relates to encoded bracelets, methods for encoding the bracelets, apparatus for reading the codes in the bracelets and methods for reading the codes in the bracelets.

2. State of the Art

All hospital patients wear identification bracelets so that hospital personnel can quickly and accurately identify the patient. Identification bracelets are attached to newborn infants almost immediately after birth so that the infant may be identified as the child of a particular mother. Infant identification bracelets are particularly necessary because the infants cannot identify themselves and because newborn infants are not familiar to their parents and are not easily distinguished from each other visually.

The typical identification bracelets utilized for both adults and infants in hospitals are clear plastic straps which have a pocket (or opaque straps with a clear pocket) in which a printed paper is inserted. The pockets are not wholly transparent, but usually have a milky translucence which makes it difficult to read the printed paper contained in the strap. In addition, the printed paper is often printed poorly which makes reading the information printed thereon difficult, especially in low light conditions.

It is well known that hospital staff members often mistakenly associate an infant with the wrong parents. This usually happens because the identification bracelet on the infant is difficult to read or because the hospital staff member confuses two infants. Sometimes newborn infants are incorrectly identified by hospital staff members and then presented to the wrong mother for nursing. In a recent incident which was widely reported in the news media, an infant infected with the HIV virus was mistakenly given to the wrong mother for nursing. There have also been cases where a newborn infant was released from the hospital in the custody of the wrong parents. While it is believed that most of the incidents of mistaken infant identity are eventually recognized, current identification procedures do not provide any reliable basis for assuring that infants are correctly identified or even for indicating when an infant has been incorrectly identified. In other words, with the procedures in use today, a mis-match of a mother and infant during nursing could go completely undetected.

In addition to the incidents of mistaken identity, there have been many incidents of willful deception in which infants have been abducted or exchanged with another infant. While most abducted infants are eventually recovered, some are not. With the present identification procedures, it is impossible to know how many incidents of exchanged infants are never discovered.

SUMMARY OF THE INVENTION

It is therefore an object of the invention to provide identification bracelets for infants and parents which allow for a positive identification of infants and parents.

It is also an object of the invention to provide identification bracelets for infants and parents which contain several identification data for matching the bracelets of parents and infants.

It is another object of the invention to provide identification bracelets for infants and parents which contain identification data which can be positively read in low light conditions.

It is still another object of the invention to provide identification bracelets for infants and parents which contain identification data which cannot be altered without authorization.

It is also an object of the invention to provide identification bracelets for infants and parents which contain identification data which can only be read by authorized persons.

It is another object of the invention to provide an apparatus for writing identification data on identification bracelets for infants and parents which prevents errors.

It is still another object of the invention to provide an apparatus for reading identification data on identification bracelets for infants and parents which provides a record of each attempted matching of an infant bracelet with a parent bracelet.

It is also an object of the invention to provide an apparatus for reading identification data on identification bracelets for infants and parents which provides correct readings in low light conditions.

It is yet another object of the invention to provide an apparatus for reading identification data on identification bracelets for infants and parents which provides both audible and visual indications of the data read.

It is another object of the invention to provide a method of writing identification data on identification bracelets for infants and parents which prevents errors.

It is still another object of the invention to provide a method of reading identification data on identification bracelets for infants and parents which provides a record of each attempted matching of an infant bracelet with a parent bracelet.

It is also an object of the invention to provide a method for reading identification data on identification bracelets for infants and parents which provides correct readings in low light conditions.

It is yet another object of the invention to provide a method for reading identification data on identification bracelets for infants and parents which provides both audible and visual indications of the data read.

In accord with these objects which will be discussed in detail below, a parent-infant identification system according to the invention includes a matched set of three bracelets each bearing matching visual indicia and data which cannot be read without the aid of a data reading apparatus, and a data reading apparatus. Two of the three bracelets are sized to fit adult wrists and the third bracelet is sized to fit an infant wrist or ankle. In a presently preferred embodiment, two infant bracelets are provided, one for the wrist and one for the ankle. The matching visual indicia includes a serial number imprinted on the bracelet and preferably also includes a color code. In the presently preferred embodiment, the data which cannot be read without the aid of a data reading apparatus are contained in "data buttons". The data buttons each contain electronically readable data which allows the data buttons to be identified with a data button reader. The data button reader includes matching apparatus for determining whether the data button on one bracelet matches the data button on another bracelet, signal apparatus for signalling whether or not the data buttons match, and recording apparatus for recording the results of each reading transaction.

According to the invention, the data which cannot be read without the aid of a data reading apparatus are unique to each bracelet, but are related to each other such that a match determination can be made upon reading the data from two bracelets. For example, the data on the infant bracelet is derived as a function of the data on each of the parent bracelets.

According to a presently preferred embodiment of the invention, the electronically readable data in each data button includes data which identifies whether the button is attached to a parent bracelet or an infant bracelet. The data button on the infant bracelet contains matching data for matching the infant bracelet with the parent bracelets and the matching data is preferably encrypted. The data buttons on the parent bracelets each includes the matching data for matching them with the infant bracelet data button as well as password data needed for reading the encrypted data on the infant data button.

The presently preferred embodiment of the data button reading apparatus includes an audible signal apparatus which produces at least three distinctive audible signals: a signal which indicates a successful reading of a data button, a signal which indicates a successful matching of two data buttons, and a signal which indicates that two read data buttons do not match. Preferably, a fourth audible signal is produced to indicate a reading error. In a presently preferred embodiment, a fifth audible signal is produced upon a 15–30 second time out between button reads. The recording apparatus in the data button reading apparatus preferably includes a time and date stamping apparatus which records the time and date of each button reading and the results of the attempted match of two data buttons.

According to the presently preferred methods of the invention, the infant data button contains encrypted information and cannot be read without having obtained the password data from a parent data button.

Additional objects and advantages of the invention will become apparent to those skilled in the art upon reference to the detailed description taken in conjunction with the provided figures.

BRIEF DESCRIPTION OF THE DRAWINGS

FIGS. 8a through 8f illustrate an alternative embodiment of the invention wherein unique bar code data is provided on each of the parent and infant bracelets.

DETAILED DESCRIPTION OF THE PREFERRED EMBODIMENTS

Figure 1:
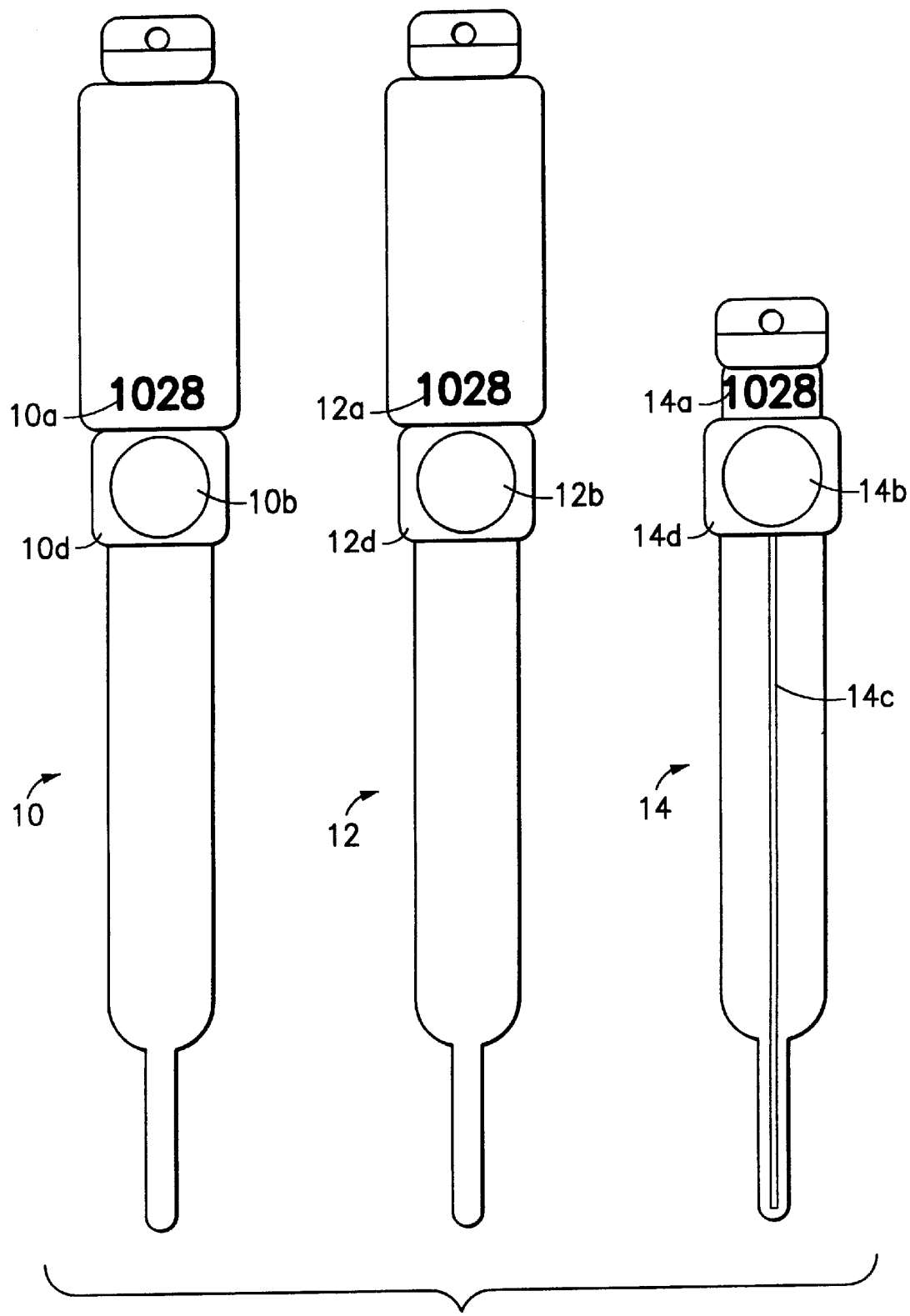
FIG. 1 is a plan view of a matched set of parent and infant identification bracelets according to the invention.

Referring now to FIG. 1, a parent-infant identification system according to the invention includes a matched set of two adult bracelets 10, 12, and one infant bracelet 14, each bearing matching visual indicia 10a, 12a, 14a, and an electronically readable data button 10b, 12b, 14b. As shown in FIG. 1, the visual indicia 10a, 12a, 14a includes a serial number, e.g. "1028". In addition, and as described in more detail below with reference to FIG. 8, the visual indicia also preferably includes a color coding scheme. Optionally, the infant bracelet 14 includes a micro-magnetic strip 14c such as one available from Knogo, Hauppauge, N.Y. under the trademark SUPERSTRIP. The strip is used with other equipment available from the same manufacturer for perimeter security which detects when the strip is moved outside the monitored perimeter. As mentioned above, a presently preferred embodiment of the invention may include two infant bracelets, one with a data button and one without. The data button bracelet is preferably attached to the infant's ankle.

The electronically readable data buttons 10b, 12b, 14b are of the type manufactured by Dallas Semiconductor, Dallas, Tex., under the trademarks TOUCH MEMORY and "i Button". Each data button contains a non-volatile programmable read-only memory (PROM) and an unalterable laser encoded unique 48-bit serial number with a CRC (cyclic redundancy check) code. The 48-bit serial number includes a "family code" which identifies the button as being one of several types available from the manufacturer. The buttons are available with adhesive backing.

A suitable strap for making the bracelets according to the invention is available from Precision Dynamics Corp., San Fernando, Calif. The buttons 10b, 12b, 14b are attached to the straps with plastic slides 10d, 12d, 14d to which the buttons are adhered with their adhesive backing.

Figure 2:
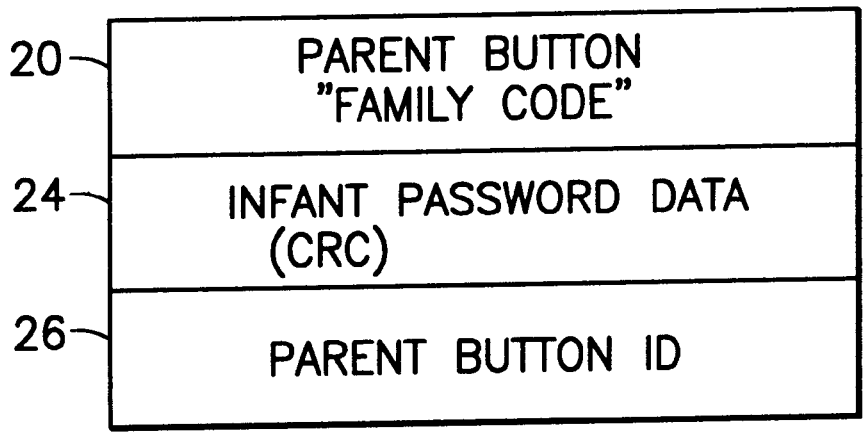
FIG. 2 is a schematic diagram of the identification data contained in a parent bracelet data button according to the invention.
Figure 3:
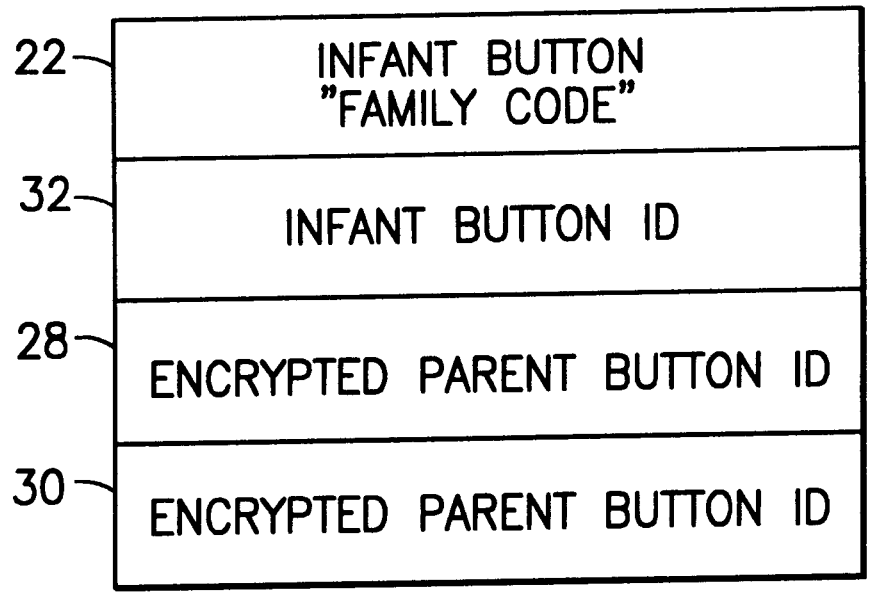
FIG. 3 is a schematic diagram of the identification data contained in an infant bracelet data button according to the invention.

Referring now to FIGS. 1–3, according to the invention, the buttons 10b, 12b used on the parent bracelets 10, 12 are selected to have the same "family code" 20 and the button 14b used on the infant bracelet 14 is selected to have a different "family code" 22. The 48-bit serial number and the CRC in the parent buttons is left unaltered, but the CRC 24 of each parent button is used as an encryption seed to encrypt the 48-bit serial number (parent button ID) 26. As described in more detail below with reference to FIG. 6, the encrypted parent button IDs 28, 30 (FIG. 3) are stored in a "write once" PROM of the infant data button for use in the identification method according to the invention.

Figure 4:
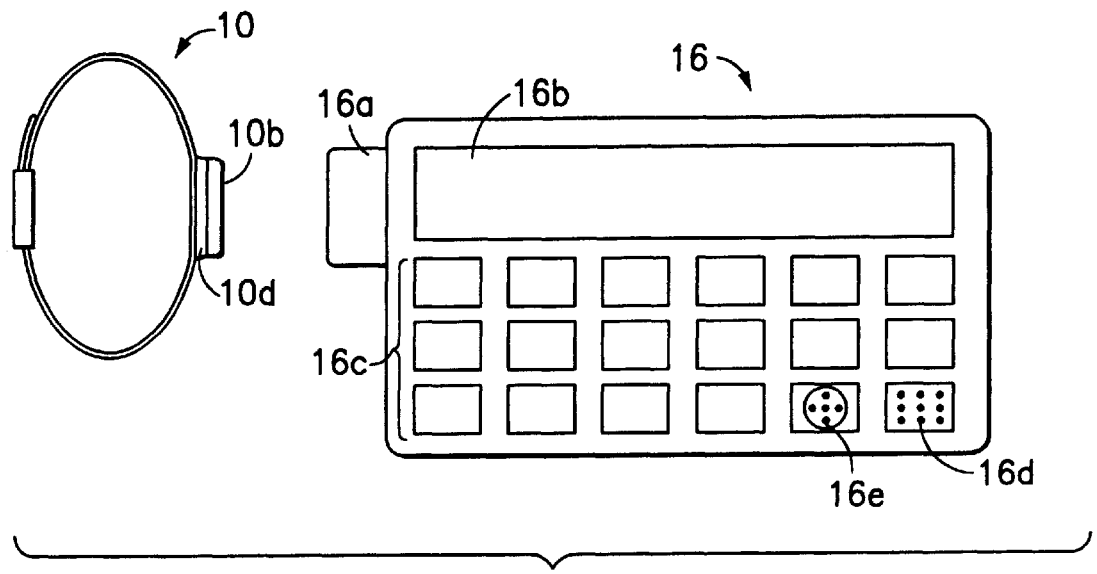
FIG. 4 is a side elevation view of a data button reader and a parent bracelet according to the invention.

Referring now to FIG. 4, the identification system according to the invention also includes a data button reader 16 which may be of the type available from either Dallas Semiconductor or Texas Instruments, Dallas, Tex. which is modified as described herein. In a presently preferred embodiment, the reader is a modified TOUCH PROBE available from Videx, Portland, Oreg. The reader 16 generally includes a probe 16a for reading the data buttons when contacting them, a visual display 16b for displaying data and prompts, and a plurality of operational keys 16c for operating the reader. According to the invention, the reader 16 is also provided with an audio transducer 16d and a download port 16e. The presently preferred modified TOUCH PROBE does not have a keypad or an alphanumeric display, and the download port is via the probe.

Figure 5:
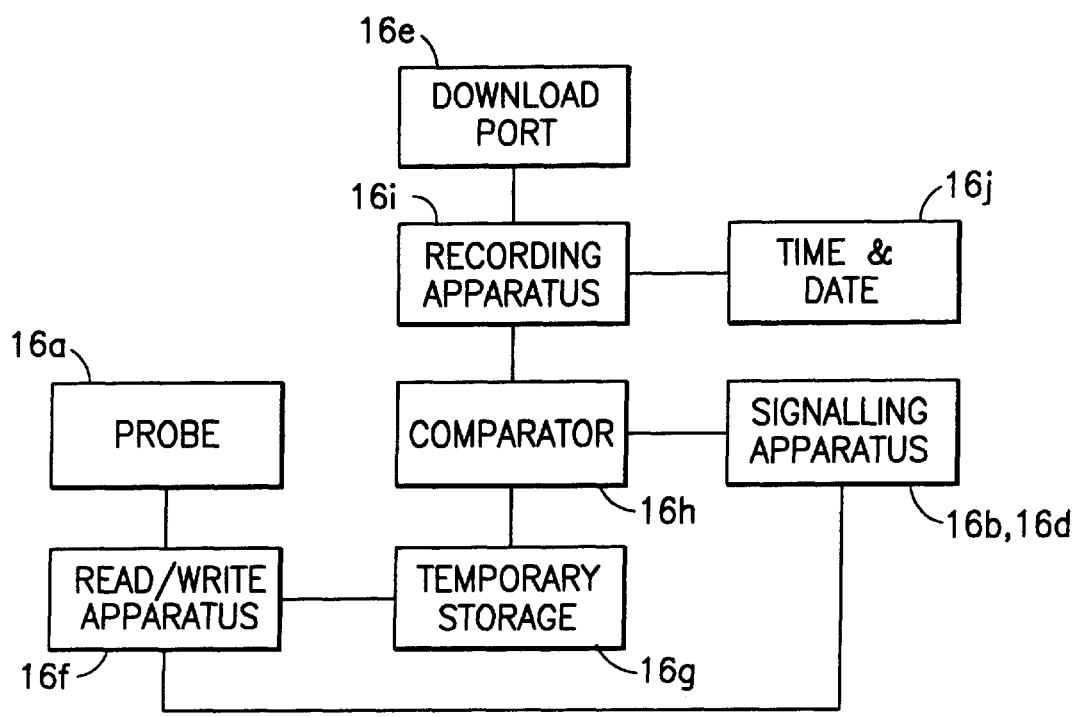
FIG. 5 is a schematic block diagram of the functional components of the data button reader of FIG. 4.

Referring now to FIG. 5, the reader 16 according to the invention also includes read/write apparatus 16*f*, temporary storage 16*g*, a comparator/processor 16*h*, a recording apparatus with non-volatile memory 16*i*, and a clock-calendar 16*j* for registering a time & date stamp. The read/write apparatus 16*f* communicates with the probe 16*a* and the temporary storage 16*g* during an identification procedure to temporarily store the data read from two data buttons for comparison by the comparator 16*h*. The identity of the data buttons and the results of the comparison (whether they be positive or negative) are recorded in nonvolatile memory by the recording apparatus 16*i* which adds a time and date stamp from the clock-calendar 16*j*. According to a method of the invention which is described in more detail below, the stored results are downloaded via the download port 16*e* to a central computer and form an "audit trail" of all attempted matchings of parents and infants. According to the invention, and as described in more detail below with reference to FIG. 7, the signalling apparatus 16*b*, 16*d* produces different signals depending on whether a button has been successfully read and whether a matching parent and infant have been identified. The functions of the reader 16 are described below with reference to FIG. 7 wherein the reading and matching methods of the invention are explained.

Figure 6:
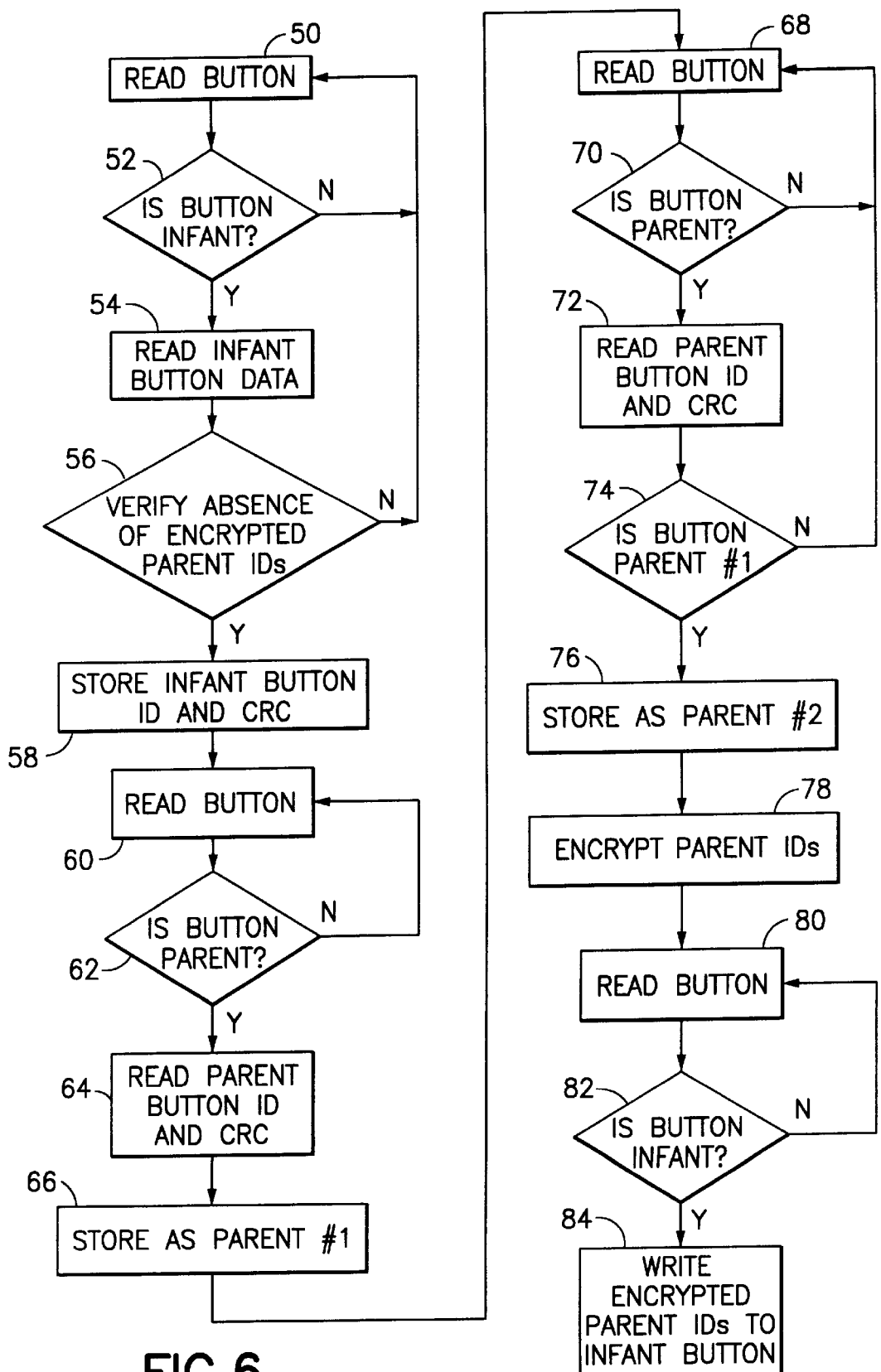
FIG. 6 is a schematic flow chart illustrating a method of encoding parent and infant data buttons according to the invention.

As mentioned above, the identification bracelet set shown in FIG. 1 is prepared such that the data button 14*b* on the infant bracelet 14 contains data relating to the parent buttons 10*b*, 12*b*. FIG. 6 illustrates a method of the invention for programming the infant data button. The programming operation may be carried out with a standard button reader/writer available from Texas Instruments or Dallas Semiconductor or may be accomplished with a personal computer and data button probe kit which is also available from Dallas Semiconductor. According to the preferred embodiment of the invention, the data buttons are programmed by the manufacturer prior to packaging so that they arrive at a health care facility ready to use without the need for programming.

Turning now to FIG. 6, the infant button is read first at 50. It is determined at 52, by reading the "family code", whether the button is one of the two parent buttons or the infant button. If the button is not an infant button, the user (manufacturer) is prompted to read the infant button first and the program returns to 50. If the button is an infant button, the data in the button (ID, CRC, and any data in PROM) is read at 54. The data is analyzed at 56 to determine whether the infant button already contains encrypted parent IDs. If the infant button was already programmed, the user is prompted and the program returns to 50. If the infant button does not contain encrypted parent IDs, the infant button ID (32 in FIG. 3) and CRC are stored at 58 for use later in the program. The user is then prompted to read a parent button at 60. The "family code" is read and it is determined whether the button is a parent button at 62. If the button is not a parent button, the user is prompted and the program returns to 60. If the button is a parent button, the ID and CRC from the parent button are read at 64 and stored at 66 with an indication that this is the first of two parent buttons. The user is then prompted to read the second parent button at 68. The "family code" is read and it is determined whether the button is a parent button at 70. If the button is not a parent button, the user is prompted and the program returns to 68. If the button is a parent button, the ID and CRC from the parent button are read at 72 and it is determined at 74 whether this parent button is the previously read "first parent button". If this button is the same previously read button, the user is prompted and the program returns to 68. If it is determined at 74 that this is the second parent button, the ID and CRC for the button are stored at 76 with an indication that this is the second of two parent buttons.

As mentioned above, the parent IDs are encrypted using the CRC as an encryption seed. According to a presently preferred embodiment, the first parent ID is encrypted using the first parent button CRC and the CRC of the infant button. Similarly, the second parent ID is encrypted using the second parent button CRC and the CRC of the infant button. The encryption takes place at 78 in FIG. 6. The user is then prompted to read the infant button at 80. The button data is compared at 82 to the button data stored at 58. If the button is not the same infant button that was read earlier, the user is prompted and the program returns to 80. If it is determined at 82 that the button is the same infant button that was read earlier, the PROM of the infant button is written with the encrypted parent IDs at 84.

Figure 6A:
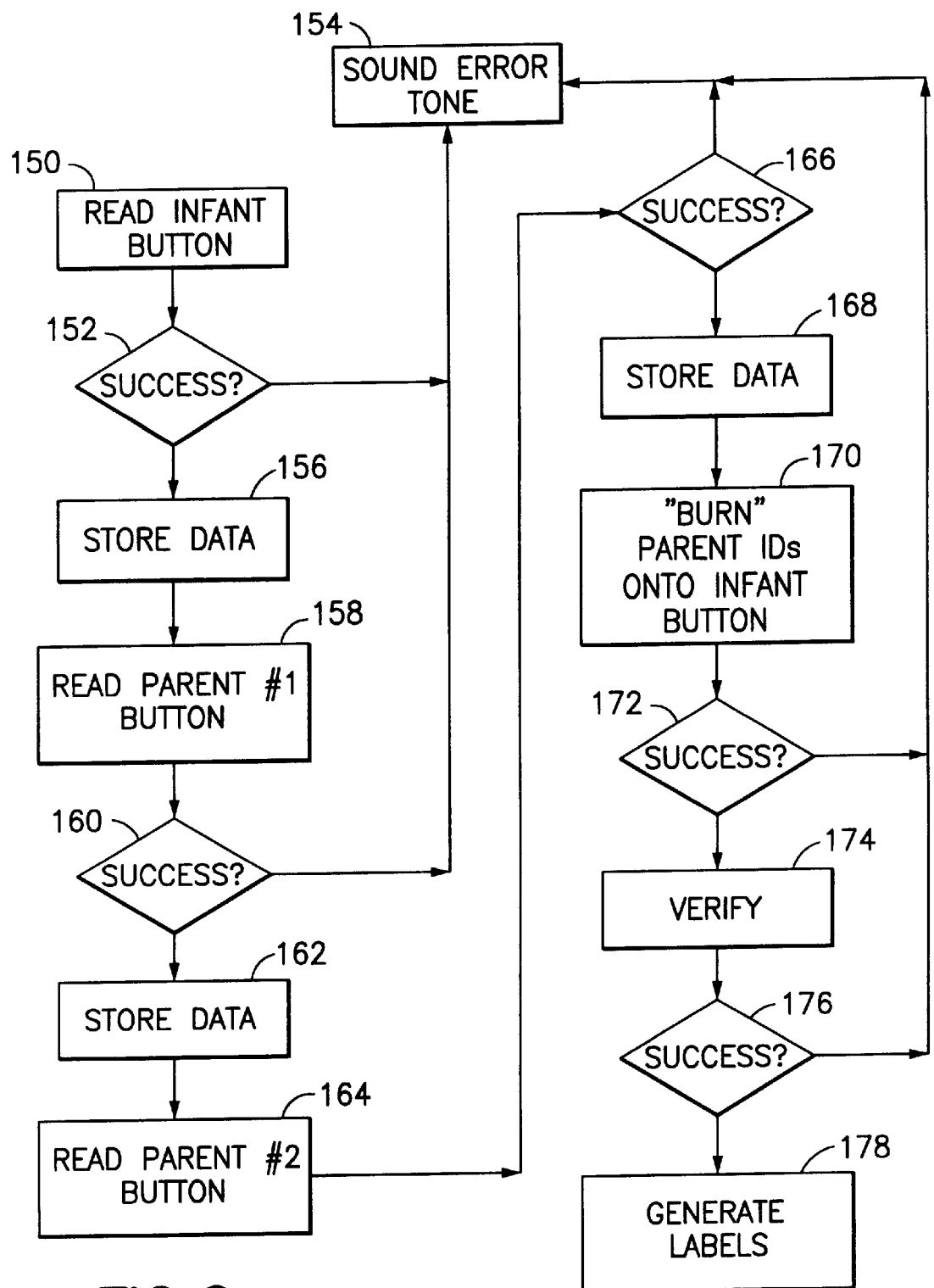
FIG. 6a is a schematic flow chart illustrating an alternative, simpler, method of encoding parent and infant data buttons according to the invention.

An alternative, simpler, programming procedure is illustrated in FIG. 6*a*. According to the procedure shown in FIG. 6*a*, the infant data button is read at 150. The data is checked at 152 to determine a successful read. If the read was not successful, an error tone is sounded at 154. Upon a successful read, the infant data is stored at 156. The first parent button is read at 158, checked at 160, and, if successfully read, stored at 162. The second parent button is read at 164, checked at 166, and, if successfully read, stored at 168. After all of the buttons have been read, the infant button is encoded with the data from both parent buttons at 170. If the encoding is completed successfully as determined at 172, the data is verified at 174 by comparing it with the data stored at 162 and 168. If it is determined at 176 that the verification failed, an error tone is generated at 154. If the verification was successful, a set of labels may be generated at 178. The labels will be packaged with the bracelet kit and used as additional indicia for matching the bracelets.

The above described programming procedure is performed during the manufacture and assembly of the identification bracelet set shown in FIG. 1. The identification bracelets 10, 12, and 14 are then packaged together in a sealed package for delivery to a health care facility with a button reader, if needed. The health care facility may already have one or more button readers if they have been using the system according to the invention. The bracelets do not require any programming by the health care facility. In the delivery room, when the infant is born, a prepackaged matched set of bracelets is opened and the infant bracelet is attached to the infant's wrist or ankle. One of the parent bracelets is attached to the mother's wrist. If the father is present, the other parent bracelet is attached to the father's wrist. If the father is not present, both parent bracelets are attached to the mother's wrist(s). Once this is accomplished, the button reader will be used every time the infant is brought to the mother or the father.

Figure 7:
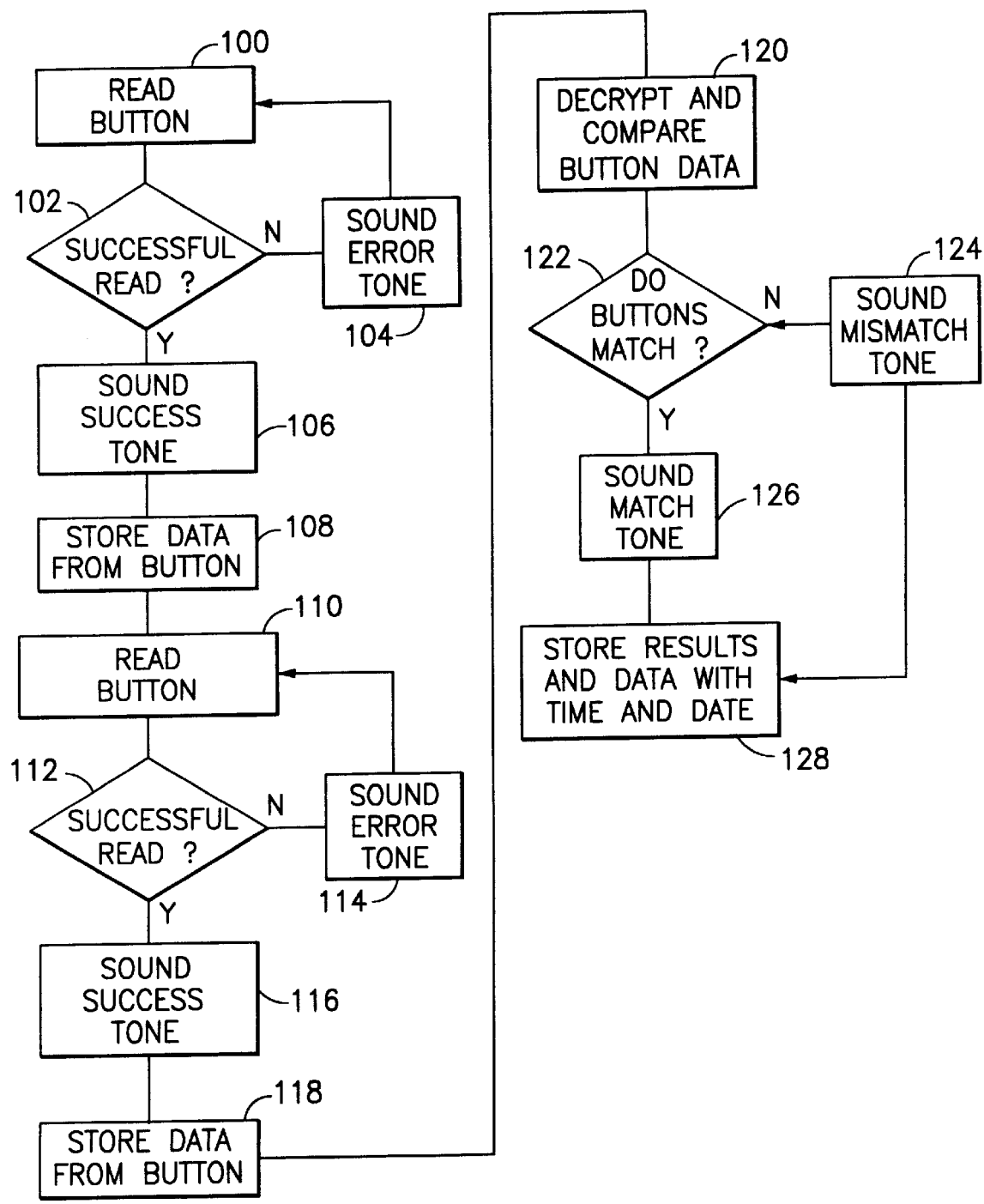
FIG. 7 is a schematic flow chart illustrating a method of reading parent and infant data buttons according to the invention.

Turning now to FIG. 7, and with reference to FIG. 4, when an infant is to be presented to a parent, the button reader 16 is placed next to a bracelet 10 and the probe 16*a* is placed in contact with the data button 10*b*. The reader is activated and the button (either a parent button or an infant button) is read at 100 in FIG. 7. The data and CRC are compared at 102 to determine whether the read was successful. If the CRC does not match the data, an error tone (e.g. "uh-oh") is sounded at 104 and the reader attempts again at 100 to read the button. If it is determined at 102 that the data was read correctly, a success tone (e.g., several notes from Hush Little Baby) is sounded at 106 and the data and CRC is stored at 108. The user (hospital or health care practitioner) is then prompted to read another button at 110. The data and CRC from the second button are compared at 112 and if the data was not correctly read, an error tone is sounded at 114. Optionally, the family codes of the first and second button are compared and if they are not different (i.e. one parent and one infant), an error tone is sounded. If the data is correctly read, and optionally of the correct type, a success tone is sounded at 116 and the data and CRC from the second button is stored at 118. Referring briefly to FIG. 5, all of the above steps are accomplished by the read/write apparatus 16*f*, the temporary storage 16*g*, and the signalling apparatus 16*b*, 16*d*.

Turning back to FIG. 7, the data stored at 108 and 118 is decrypted and compared at 120 and a determination is made at 122 whether the parent and infant buttons match. If the buttons do not match, a mismatch tone (e.g. a siren) is sounded at 124 and the transaction is recorded at 128 indicating the date and time that the mismatch occurred. If the buttons are found at 122 to match, a match tone preferably having a nursery theme (e.g., several notes from Hush Little Baby) is sounded at 126 and the transaction recorded at 128 indicating the date and time that the match was made. Referring briefly to FIG. 5, those skilled in the art will appreciate that the comparing and recording steps are accomplished by the comparator 16*h*, recording apparatus 16*i*, time & date stamp 16*j*, as well as the signalling apparatus 16*b*, 16*d*.

According to the methods of the invention, the stored transactions are downloaded from the button reader at regular intervals, such as once a day. The transactions are downloaded to a central computer which maintains an audit trail of each transaction involving the matching of a parent and an infant.

While the presently preferred embodiment of the invention stores data in data buttons, those skilled in the art will appreciate that the data may be stored in other kinds of media. An important aspect of the invention is that the data on each bracelet is unique so that a false match cannot be obtained by reading the same bracelet twice. With all of the foregoing in mind, those skilled in the art will appreciate that several aspects of the invention can be achieved with the use of bar coded data in lieu of data buttons. FIGS. 8*a* through 8*f* illustrate how the bracelets can be encoded using the CODE3OF9X1 bar code. For example, as shown in FIGS. 8*a* and 8*b*, a first parent bar code 200 represents nine digits, the first of which 202 is an indicator that the code represents a parent bracelet. The next four digits 204 represent the parent ID, and the last four digits 206 are not used. FIGS. 8*c* and 8*d* show a second parent bar code 300, representing nine digits the first of which 302 is an indicator that the code represents a parent bracelet. The next four digits 304 represent the parent ID, and the last four digits 306 are not used. FIGS. 8*e* and 8*f* show an infant bar code 400. The first digit 402 represented by the bar code 400 indicates that the bar code represents an infant bracelet and the remaining eight digits 404 represent a function of both parent IDs. In this example, the digits 404 are a concatenation of the first parent ID 204 and the second parent ID 304. Those skilled in the art will appreciate, however, that other functions could be utilized to create a unique infant ID which "points to" both of the parent IDs.

Figure 9:
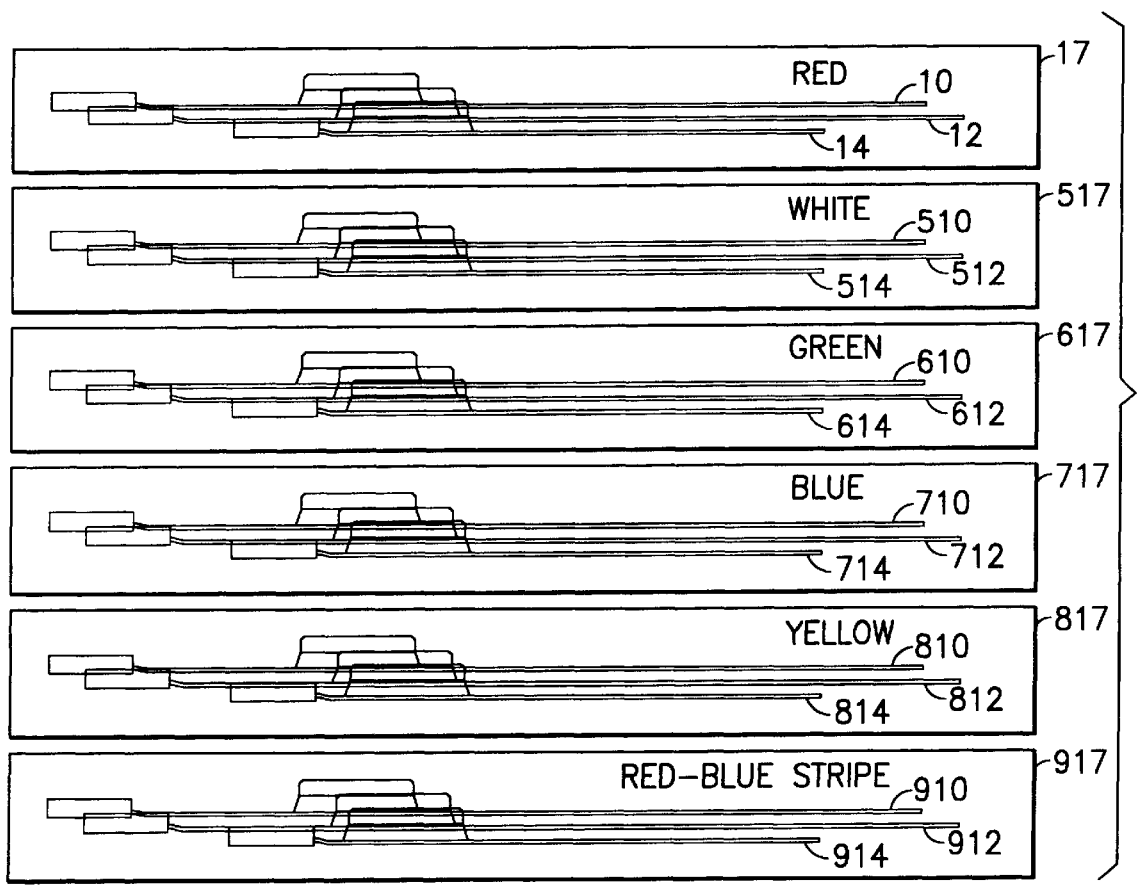
FIG. 9 is a side elevation view of a bundle of color coded identification bracelet kits according to the invention.

From the foregoing, it will be appreciated that the methods and apparatus of the invention provide a positive identification of parents and infants which will prevent inadvertent or deceptive mismatching of parents and infants. The inventive system is virtually error-free, is easy to use, provides positive feedback in low light conditions, and provides an audit trail in order to confirm that infants have not been misplaced. As mentioned above, the bracelet sets according to the invention are provided with multiple indicia as an additional confirmation that the parents and infant are from the same family and to assure that the bracelets are from the same set when they are attached to the parents and the infant. According to a presently preferred embodiment, each bracelet set is a distinctive color and a modulus of up to fifty distinctive colors/combinations is provided when shipping boxes of bracelet sets. For example, as shown in FIG. 9, a first bracelet set having three red bracelets 10, 12, 14 is packaged in a clear sealed container 17. A second bracelet set having three white bracelets 510, 512, 514 is packaged in a clear sealed container 517. A third bracelet set having three green bracelets 610, 612, 614 is packaged in a clear sealed container 617. A fourth bracelet set having three blue bracelets 710, 712, 714 is packaged in a clear sealed container 717. A fifth bracelet set having three yellow bracelets 810, 812, 814 is packaged in a clear sealed container 817. A sixth bracelet set having three red and blue striped bracelets 910, 912, 914 is packaged in a clear sealed container 917. The number of bracelet sets may vary, but according to the invention, they are packed so that no two consecutively packed sets have the same color. Preferably, no two sets in any box have the same color. In this manner, the likelihood that any two mothers in a maternity ward will wear bracelets of the same color is minimized and the positive identification of infants and parents is enhanced.

There have been described and illustrated herein several embodiments of an identification bracelet system for identifying parents and infants in a health care facility. While particular embodiments of the invention have been described, it is not intended that the invention be limited thereto, as it is intended that the invention be as broad in scope as the art will allow and that the specification be read likewise. Thus, while particular visual data for the bracelets have been disclosed, it will be appreciated that other visual data could also be utilized. In particular, the bracelets may be provided with a conventional label carrying pocket and a printed label may be inserted therein. Also, while plastic slides have been shown for attaching data buttons to straps, it will be recognized that other types of attachments could be used with similar results obtained. Moreover, while particular configurations have been disclosed in reference to button reader, it will be appreciated that other configurations could be used as well. Furthermore, while the button has been disclosed as having a display, it will be understood that a button reader having only audible signalling can achieve the same or similar function as disclosed herein. Further yet, different types of audible signalling can be used such as digitized speech signals, e.g. "match", "no match", "please re-read", different types of musical signals, etc. It will therefore be appreciated by those skilled in the art that yet other modifications could be made to the provided invention without deviating from its spirit and scope as so claimed.

What is claimed is:

1. A parent and infant identification system comprising:
   a) a matched set of identification bracelets, said matched set containing at least one infant identification bracelet and two parent identification bracelets, each of said bracelets bearing matching visual indicia, each of said bracelets bearing an electronically readable data button, each of said data buttons bearing matching electronically readable data; and b) an electronic data button reader for sequentially reading said data buttons, said reader including audible means for indicating when two sequentially read buttons bear matching data, wherein at least one of said electronically readable data includes means for enabling said data button reader to distinguish a double reading of one of said data buttons from a sequential reading of two data buttons bearing matching electronically readable data, wherein said electronically readable data on said electronically readable data button of a first of said two parent identification bracelets includes a first parent identification number, said electronically readable data on said electronically readable data button of a second of said two parent identification bracelets includes a second parent identification number different from said first parent identification number, and said infant identification bracelet bears an electronically readable data button bearing electronically readable data which includes encrypted indications of each of said parent identification numbers.

2. An identification system according to claim 1, wherein:
said distinguishing means includes an indication of whether said data button is attached to a parent bracelet or an infant bracelet.

3. An identification system according to claim 1, wherein:
said visual indicia includes a color code.

4. An identification system according to claim 1, wherein:
said visual indicia includes one of a serial number and a color code.

5. A parent and infant identification system, comprising:
a) a matched set of identification bracelets, said matched set containing at least one infant identification bracelet and at least one parent identification bracelet, each of said bracelets bearing matching visual indicia, each of said bracelets bearing an electronically readable data button, each of said data buttons bearing matching electronically readable data; and b) an electronic data button reader for sequentially reading said data buttons, said reader including audible means for indicating when two sequentially read buttons bear matching data, wherein at least one of said electronically readable data includes means for enabling said data button reader to distinguish a double reading of one of said data buttons from a sequential reading of two data buttons bearing matching electronically readable data, said parent identification bracelet bears an electronically readable data button bearing matching electronically readable data which includes a parent identification number, said infant identification bracelet bears an electronically readable data button bearing matching electronically readable data which includes an indication of said parent identification number, and said indication of said parent identification number is in encrypted form.

6. An identification system according to claim 5, wherein:
said parent identification bracelet bears an electronically readable data button bearing matching electronically readable data which includes password data for decrypting said parent identification number in encrypted form.

7. An identification system according to claim 5, wherein:
each of said parent identification bracelets bears an electronically readable data button bearing matching electronically readable data which includes password data for decrypting its parent identification number in encrypted form.

8. A parent and infant identification bracelet set for use with an electronic data button reader, said bracelet set comprising:

a) an infant bracelet bearing first visual indicia and a first electronic data button bearing first electronically readable data; and b) a first parent bracelet bearing second visual indicia and a second electronic data button bearing second electronically readable data, wherein at least one of said electronically readable data includes means for enabling the data button reader to distinguish a double reading of a single data button from a sequential reading of first and second data buttons, wherein said first electronically readable data includes an indication of said second electronically readable data, and said indication of said second electronically readable data is in encrypted form.

9. An identification bracelet set according to claim 8, wherein:
one of said electronically readable data includes an indication of whether said data button is attached to a parent bracelet or an infant bracelet.

10. An identification bracelet set according to claim 8, wherein:
said second electronically readable data includes password data for reading said second electronically readable data in encrypted form.

* * * * *